US009801616B2

(12) United States Patent
Wallack et al.

(10) Patent No.: US 9,801,616 B2
(45) Date of Patent: Oct. 31, 2017

(54) LIVE FEED ULTRASOUND VIA INTERNET STREAMING

(76) Inventors: Seth Wallack, San Diego, CA (US); David Winter, San Diego, CA (US)

(*) Notice: Subject to any disclaimer, the term of this patent is extended or adjusted under 35 U.S.C. 154(b) by 279 days.

(21) Appl. No.: 13/085,730

(22) Filed: Apr. 13, 2011

(65) Prior Publication Data
US 2011/0249125 A1    Oct. 13, 2011

(51) Int. Cl.
| G01S 15/89 | (2006.01) |
| A61B 8/00 | (2006.01) |
| H04N 7/18 | (2006.01) |
| G06F 19/00 | (2011.01) |

(52) U.S. Cl.
CPC ............ *A61B 8/565* (2013.01); *H04N 7/183* (2013.01); *G06F 19/321* (2013.01); *G06F 19/3418* (2013.01)

(58) Field of Classification Search
None
See application file for complete search history.

(56) References Cited

U.S. PATENT DOCUMENTS

| 5,585,850 A * | 12/1996 | Schwaller ................ 375/240.01 |
| 6,972,786 B1 * | 12/2005 | Ludwig ...................... 348/14.11 |
| 2004/0267116 A1 * | 12/2004 | Flood et al. ................... 600/437 |
| 2008/0259841 A1 * | 10/2008 | Deshpande .................... 370/328 |
| 2009/0058983 A1 * | 3/2009 | Whited et al. ............. 348/14.01 |
| 2009/0228766 A1 * | 9/2009 | Djordjevic et al. .......... 714/780 |
| 2010/0070417 A1 * | 3/2010 | Flynn et al. ..................... 705/51 |
| 2010/0091841 A1 * | 4/2010 | Ishtiaq et al. ............. 375/240.02 |
| 2010/0103270 A1 * | 4/2010 | Polit et al. ..................... 348/187 |
| 2011/0134203 A1 * | 6/2011 | Smelyansky et al. ..... 348/14.01 |

OTHER PUBLICATIONS

Pyke et al., A Tele-ultrasound System for Real-time Medical Imaging in Resource-limited Settings, Preccedings of the 29th Annual International Conference of the IEEE EMBS Cite Internationale, pp. 3094-3097, Aug. 26, 2007.*
"The PortaBella BBNA", Mushroom Networks; http://www.mushroomnetworks.com/internal/brochure_PortaBella_BBNA2241.pdf, Nov. 23, 2009.*
Pederson et al., "Telemedicine Applications of Mobile Ultrasound", IEEE International Workshop on Multimedia Signal Processing, 2009. MMSP '09 , Oct. 7, 2009.*

* cited by examiner

*Primary Examiner* — James M Anderson, II
(74) *Attorney, Agent, or Firm* — San Diego IP Law Group; Trevor Coddington

(57) ABSTRACT

The present invention provides, in at least one embodiment, a system and method for real time evaluation of ultrasound video images taken at a first local location and evaluated at a second remote location. The system transmits a continuous live video feed from a veterinary ultrasound at the first location to a viewer at the remote location for real time study, review, and collaboration. In the method, the ultrasound video images are converted from analog ultrasound video to digital ultrasound video, where the digital ultrasound video is processed into multiple streams and transmitted across multiple broadband channels, each channel carrying a different stream. The multiple streams are aggregated into a reconstituted video and displayed for evaluation at the remote location.

18 Claims, 5 Drawing Sheets

LIVE FEED ULTRASOUND VIA INTERNET STREAMING

BACKGROUND OF THE INVENTION

1. Field of Invention

The present invention relates to medical imaging acquisition systems and telemedicine, and more specifically, to a technique, system, and process for transmitting and displaying ultrasound video images acquired from subjects located remotely in real time or near real time.

2. Description of Related Art

Ultrasound is cyclic sound pressure with a frequency greater than the upper limit of human hearing. Although this limit varies from person to person, it is approximately 20 kilohertz (20,000 hertz) in healthy, young adults and thus, 20 kHz serves as a useful lower limit in describing ultrasound. The production of ultrasound is used in many different fields and generally involves penetrating a medium and measuring the reflection signature. The reflection signature can reveal details about the inner structure of the medium. The most well known application of ultrasound is its use in sonography to produce pictures of fetuses in the human womb.

Medical sonography (or "ultrasonography") is an ultrasound-based diagnostic medical imaging technique used to visualize muscles, tendons, and many internal organs, to capture their size, structure and any pathological lesions with real time tomographic images. Ultrasound has been used by sonographers to image the human body for at least 50 years and has become one of the most widely used diagnostic tools in modern medicine. The technology is relatively inexpensive and portable, especially when compared with other techniques, such as magnetic resonance imaging (MRI) and computed tomography (CT).

Veterinary radiologists currently travel from site to site performing ultrasound procedures. There is currently no effective and efficient means for a veterinary radiologist to remotely oversee an ultrasound study in a real time fashion. Many conventional systems for ultrasound image transmission require still images or relatively short ultrasound video clips to be transmitted over a local access network (LAN) line. However, there is currently no technology in place to transmit a continuous live video feed from a veterinary ultrasound to a remote viewer for real time study review and collaboration.

A few prior approaches have attempted to utilize satellite technology and/or standard land-based phone lines to deliver ultrasound images and/or video in a real-time fashion. However, there are several disadvantages with implementing such systems. First, satellite transmission time is cost prohibitive. For example, satellite bandwidth typically costs $5 per minute during transmission and the initial setup of a satellite link at a particular location can be approximately $3,000-$5,000—far exceeding the cost of an ultrasound procedure itself Second, in conventional land-based phone lines utilizing a digital subscriber line (DSL), the data transmission speed is not adequate enough to transmit real-time ultrasound video. Third, the dependability of satellite technology is intermittent at best. Fourth, a satellite based system does not lend itself to efficient portability as a satellite transceiver, i.e., dish and related electronics typically requires a mounting surface and a large space to use. Fifth, satellite transceivers require an unimpeded line of sight with the satellite and knowledge of operating parameters of the satellite.

SUMMARY OF THE INVENTION

The present invention overcomes these and other deficiencies of the prior art by providing an ultrasound video transmission system to remotely oversee ultrasound studies performed in the field by medical professionals such as, but not limited to veterinary sonographers.

In an embodiment of the invention, a method for transmitting a real time ultrasound video feed comprises the steps of: acquiring an analog ultrasound video of a subject at a first location; converting the analog ultrasound video to a digital ultrasound video; processing the digital ultrasound video into multiple streams; transmitting the multiple streams over multiple broadband channels, each broadband channel carrying a different stream; aggregating the multiple streams into a reconstituted ultrasound video; and making the reconstituted ultrasound video available for display to an evaluator located at a location remote from the first location. The analog ultrasound video may be formatted according to a VGA format and the digital ultrasound video may comprise an AVI formatted video or a QuickTime formatted video. The step of processing the digital ultrasound video into multiple streams may be performed by a broadband bonding network appliance. The step of aggregating the multiple streams into a reconstituted ultrasound video may be performed by a broadband bonding network appliance. The broadband channels may comprise at least one cellular channel. The step of making the reconstituted ultrasound video available for display may be performed by a web server.

In another embodiment of the invention, a method for transmitting a video feed comprises the steps of: acquiring a video feed; processing the video feed into multiple video streams; transmitting the multiple video streams over multiple broadband channels, each broadband channel carrying a different video stream; aggregating the multiple video streams into a reconstituted video; and making the reconstituted video available for display online. The acquired video feed may be an analog video feed and further comprising the step of converting the analog video feed into a digital video feed. The multiple video streams may comprise multiple digital video streams. The reconstituted video may comprise an ultrasound video.

In another embodiment of the invention, a system comprises: a computer configured to acquire an analog ultrasound video of a subject at a first location and convert the analog ultrasound video to a digital ultrasound video; a network transceiver configured to process the digital ultrasound video into multiple streams and transmit the multiple streams over multiple broadband channels, each broadband channel carrying a different stream; a network server configured to aggregate the multiple streams into a reconstituted ultrasound video; and a web server configured to make the reconstituted ultrasound video available for display to an evaluator located at a location remote from the first location. The network transceiver may comprise a WiFi router, and the WiFi router may implement a IEEE 802.11 communications protocol. The network transceiver may comprise a broadband bonding network appliance, and the broadband bonding network appliance may comprise multiple broadband data cards, the multiple broadband data cards comprising at least one 3G modem. The system may further comprise a switch for bypassing the broadband bonding network appliance. The network transceiver may comprise data storage. The network server may comprise a broadband bonding network appliance.

An advantage of the invention is that it facilitates near real-time evaluation (approximate 2 second delay) of ultrasound video images from any remote location that has either a LAN network or standard cellular coverage. Currently, only static ultrasound images or relatively short video clips can be transmitted either during or following completion of an ultrasound examination. The present invention permits an ultrasonographer at one location to interact in near real-time with an evaluator at a second location without large infrastructure costs. The present invention is ideal since it will allow data transmission at speeds faster than DSL without requiring a LAN line.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

DETAILED DESCRIPTION OF EMBODIMENTS

Figure 1:
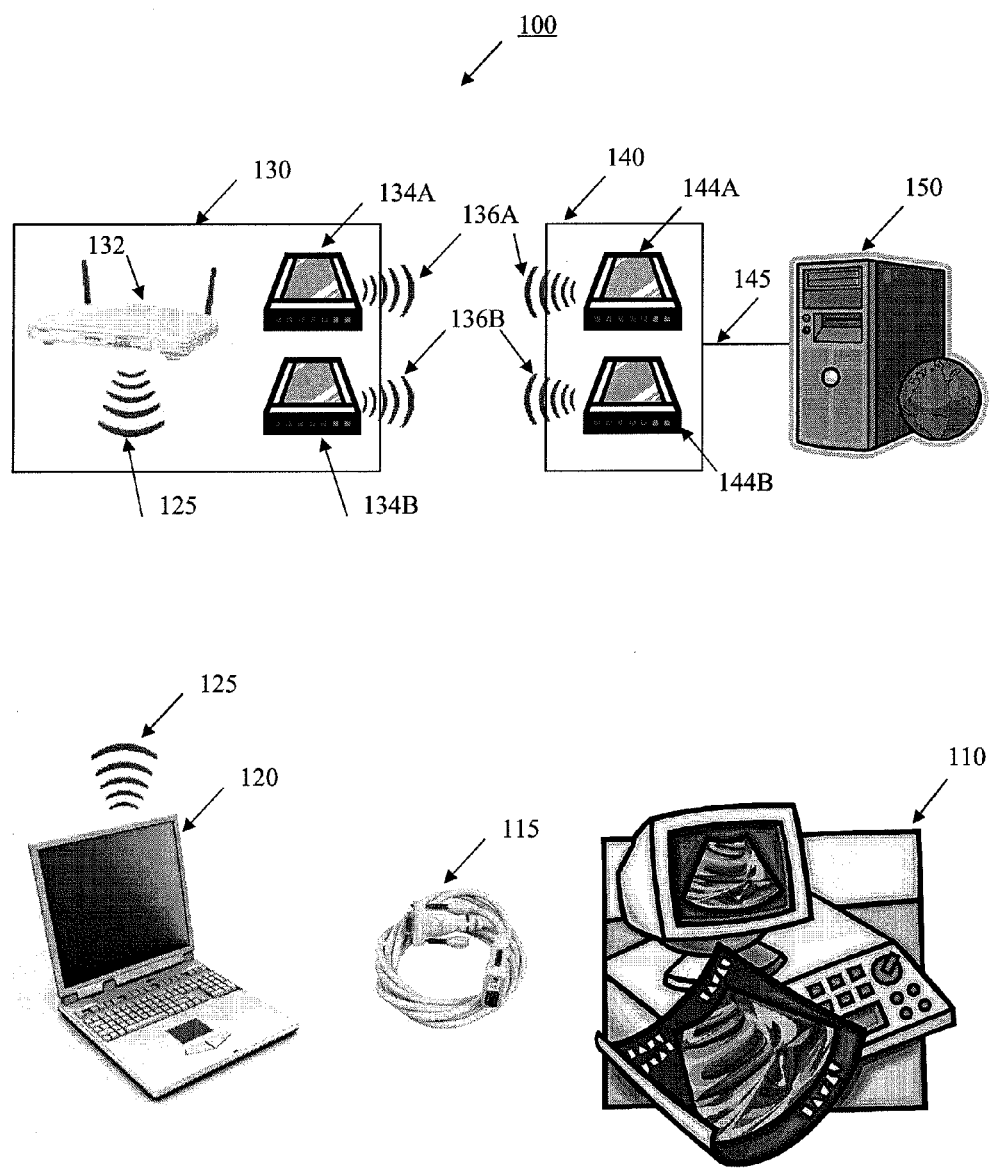
FIG. 1 illustrates an ultrasound imaging and transmission system according to an embodiment of the invention.

Further features and advantages of the invention, as well as the structure and operation of various embodiments of the invention, are described in detail below with reference to the accompanying FIGS. 1-5, wherein like reference numerals refer to like elements. Although the present invention is described in the context of ultrasound video transmission in veterinarian applications, one of ordinary skill in the art readily appreciates that the present invention can be practiced with any type of subject including human patients and is applicable to any type of telemedicine implementation where it is desired to transmit near real time video feeds acquired from a subject at one location to an evaluator located at a remote second location. The use of the term "ultrasound" in this application is intended to include all applications of ultrasound including ultrasonography.

The present invention provides a system and method for real time evaluation of ultrasound video images taken at a first local location and evaluated at a second remote location. The system transmits a continuous live video feed from a veterinary ultrasound at the first location to a viewer at the remote location for real time study, review, and collaboration. In the method, the ultrasound video images are converted from analog ultrasound video to digital ultrasound video, where the digital ultrasound video is processed into multiple streams and transmitted across multiple broadband channels, each channel carrying a different stream. The multiple streams are aggregated into a reconstituted video and displayed for evaluation at the remote location.

FIG. 1 illustrates an ultrasound imaging and transmission system 100 according to an embodiment of the invention. The ultrasound imaging and transmission system 100 comprises an ultrasound system 110, a computer 120, a network transceiver 130, a network server 140, and a web server 150. The ultrasound system 110 can be any type of conventional ultrasound machine, the identification and implementation of which is apparent to one of ordinary skill in the art, for acquiring ultrasound images and video from a subject. In a preferred embodiment of the invention, the ultrasound system 110 is compact and portable in order for the ultrasound system 110 to be easily transported to various sites. For example, the Biosound Esaote, Inc. MyLab® 30 CV is a compact and portable ultrasound system that can be employed as ultrasound system 110. However, the present invention can just as easily be practiced with a relatively older, bulky ultrasound system employed at a fixed location.

A typical ultrasound system 110 comprises a hand-held probe (not shown), which includes a piezoelectric transducer for producing a diagnostic ultrasound wave. The ultrasound system 110 further includes an analog video output (not shown) such as, but not limited to a video graphics array (VGA) standard output implementing a 15 pin D-subminiature VGA connector, which is a common type of video output found in conventional ultrasound systems. Nonetheless, one of ordinary skill in the art appreciates that other types of video outputs can be implemented in the ultrasound system 110. The analog video output of the ultrasound machine 110 is connected via a VGA cable 115 to a corresponding video input of the computer 120. In the event that the ultrasound system 110 utilizes a video output other than VGA, the format of that output can be converted to VGA through an appropriate VGA adapter or coupled to an appropriate video input of the laptop 120 either directly or through one or more adapters, the implementation of which is apparent to one of ordinary skill in the art.

The computer 120 is preferably provided in a portable form factor such as a laptop. However, the computer 120 can be any type of computing device with sufficient processing and memory resources to handle the processing and transmission of VGA video, the identification and implementation of which is apparent to one of ordinary skill in the art. In another embodiment of the invention, the computer 120 may take the form of a desktop computer, netbook computer, workstation computer, a tablet, a smartphone, etc. The computer 120 comprises hardware and/or software for converting the VGA video acquired from the ultrasound machine 110 into a digital video stream such as, but not limited to an audio video interleave (AVI) or QuickTime stream, the implementation of which is apparent to one of ordinary skill in the art. In an embodiment of the invention, the computer 120 comprises an external analog-to-digital video conversion device, e.g., VGA2USB by Epiphan Systems, Inc., for converting the analog video feed from the ultrasound system 110 into a digital video feed for delivery to a USB input of the computer 120. Alternatively, analog-to-digital video conversion functionality is integrated internally within the computer 120 using, for example, an internal peripheral component interconnect (PCI) card that utilizes the internal power supply of the computer.

The computer 120 further comprises a communications card (not shown) for transmitting the digital ultrasound video stream to the network transceiver 130. In a preferred embodiment of the invention, the communications card implements a wireless communications protocol standard such as, but not limited to the Institute of Electrical and Electronic Engineers (IEEE) 802.11(n), the implementation of which is apparent to one of ordinary skill in the art. IEEE 802.11 refers to the family of wireless protocols commonly known as WiFi. 802.11(n) communications links operate at data transmission speeds up to 70 Mbs, which is 70 times faster than a 802.11(g) link. The communications card transmits the digitized ultrasound video stream to the network transceiver over a wireless communication link 125 such as 802.11(n). However, any communications protocol can be implemented in the communications card including wired communications protocols such as, but not limited to Ethernet.

The network transceiver 130 comprises a router 132 for communicating with the computer 120. The router 132 preferably implements the IEEE 802.11(n) communications standard or whatever standard is being implemented by the communications card of the computer 120. The network transceiver 130 further comprises a broadband bonding network appliance comprising a number of broadband modems 134A-N (although only two are shown for illustration purposes) that receive the digitized video data from the router 132 and transmit such to the network server 140 through aggregated broadband channels 136A-N (although only two are shown for illustration purposes). In an exemplary embodiment of the invention, the broadband modems 134A-N are cellular aircards associated with public data carriers (e.g., Verizon, Sprint, Cricket, Alltel, T-Mobile, Virgin, AT&T, etc.) to create a fast and reliable communications link. The broadband bonding network appliance is capable of binding these multiple cellular channels allowing for higher data throughput by utilizing data binding technology to split the data across all available wireless networks. See, e.g., U.S. Patent Application Publication No. 2008/0267184 to Arisoylu, entitled "Link Aggregation Methods and Devices," the disclosure of which is incorporated by reference herein in its entirety.

The network transceiver 130 may optionally include data storage such as, but not limited to a USB storage card (not shown), for storing ultrasound video transmitted to the router 132 from the computer 120. A single toggle switch (not shown) may be included in the network transceiver 130 to alternate between data storage (on the USB storage card) and data upload (to the web server 150) modes. In another embodiment of the invention, the ultrasound system 110, the computer 120, the network transceiver 130, or any subcombination thereof may be combined into a single form factor.

In another embodiment of the invention, the network transceiver 130 comprises a twisted pair high signal integrity cable input for connecting the laptop 120 to the network transceiver 130 via a Category 5 or Category 6 cable, the implementation of which is apparent to one of ordinary skill in the art. In this scenario, the laptop 120 and network transceiver 130 are able to communicate using a wired communications protocol such as, but not limited to Ethernet.

In another embodiment of the invention, the cellular channels 136A-N can be bypassed if a reliable and high speed internet connection is available. Here, the network transceiver 130 comprises two CAT 5 or CAT 6 connections (not shown). One CAT 5 or CAT 6 connection attaches to the broadband modems 134A-N and the other CAT 5 or CAT 6 connection attaches to the wireless router 132. In an embodiment of the invention, in order to utilize the broadband channels 136A-N, a single CAT 5 or CAT 6 cable (not shown) is used to bridge the connection between the router 132 and the broadband modems 134A-N. When an external high-speed internet connection is available, the CAT 5 or CAT 6 cable is not connected between the router 132 and the broadband modems 134A-N. In the latter scenario, an additional and separate CAT 5 or CAT 6 cable is used to connect the internal router 132 to the external high-speed internet connection.

The network server 140 comprises a broadband bonding network appliance including a number of broadband modems 144A-N (although only two are shown for illustration purposes). The broadband bonding network appliance reassembles the data received across the broadband channels 136A-N used by the network transceiver 130. The network server 140 is coupled to the web server 150 through an appropriate data connection 145 such as a transmission control protocol/internet protocol (TCP/IP) connection. In a related embodiment of the invention, the network server 140 and web server 150 can be combined as one server located at a single location.

The web server 150 acts an Internet server for facilitating the display of the ultrasound video received from the network transceiver 130 to an evaluator located at any location with a high-speed internet connection. In an embodiment of the invention, the web server 150 comprises a web server application, the identification and implementation of which is apparent to one of ordinary skill in the art, for delivering the ultrasound video to a computer of the evaluator executing an appropriate web browser or the like. In an embodiment of the invention, the web server 150 requires the evaluator to authenticate his computer and/or identification before being permitted to view the ultrasound video stream.

Figure 2:
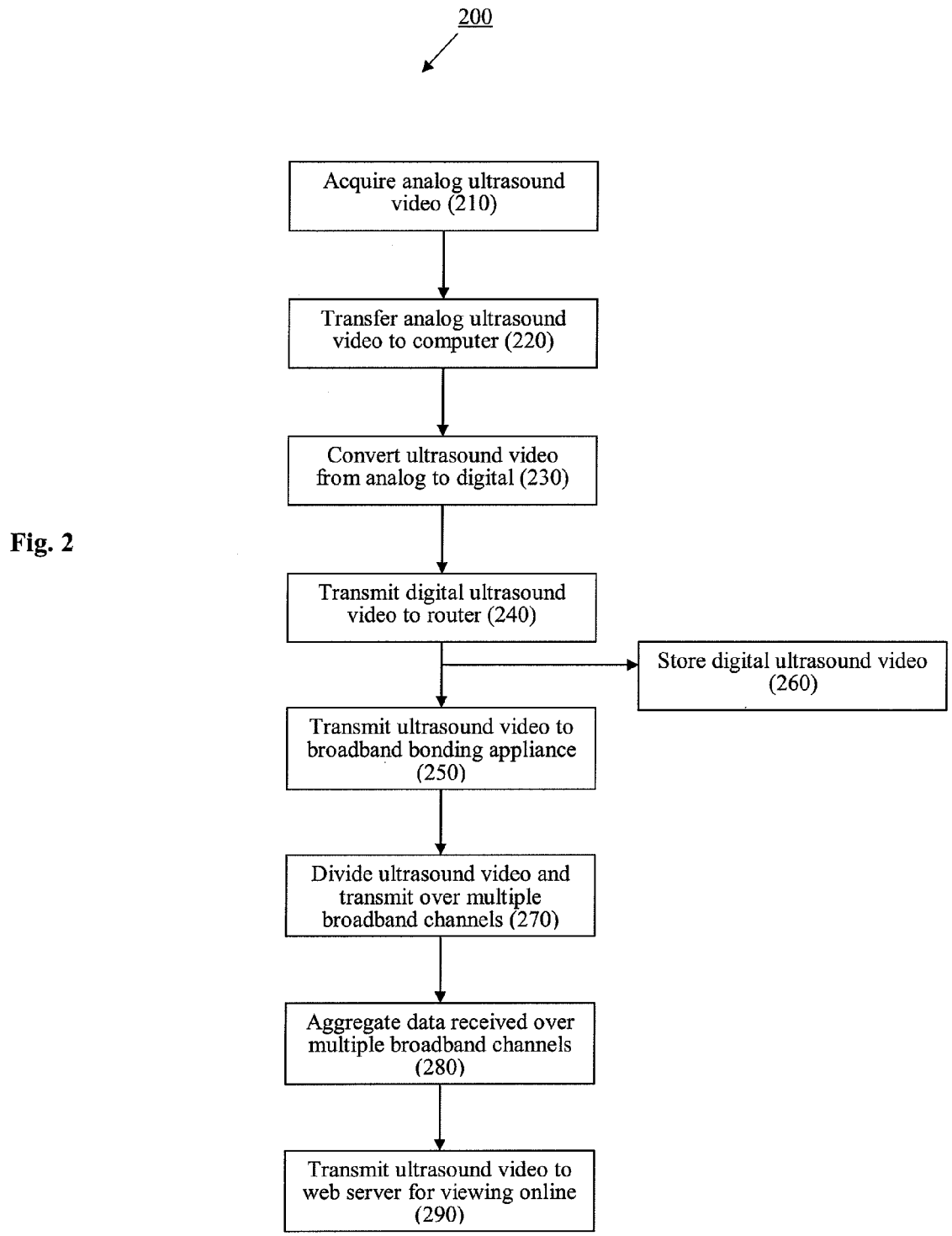
FIG. 2 illustrates an ultrasound transmission process according to an embodiment of the invention.

FIG. 2 illustrates an ultrasound transmission process 200 according to an embodiment of the invention. The ultrasound transmission process 200 begins by acquiring (step 210) an analog ultrasound video of a patient at the ultrasound system 110. The analog ultrasound video is transferred (step 220) from the ultrasound system 110 to the computer 120 via a suitable analog video connector or transmission medium, e.g., VGA cable. The computer 120 converts (step 230) the analog video into a digital video stream. The digital video stream is then transmitted (step 240) to the router 132 of the network transceiver 130. The router 132 transmits (step 250) the digital video stream to the broadband bonding network appliance and/or stores (step 260) the digital video stream to a local USB storage device. The broadband bonding network appliance transmits (step 270) the digital video stream over multiple broadband channels to the network server 140. The network server 140 aggregates (step 280) the data received over the multiple broadband channels into a single digital video stream, which is then transmitted (step 290) to a web server 150 where the digital video stream can be viewed by an evaluator online.

It is to be recognized that depending on the embodiment, certain acts or events of any of the methods described herein can be performed in a different sequence, may be added, merged, or left out altogether (for example, not all described acts or events are necessary for the practice of the method). Moreover, in certain embodiments, acts or events may be performed concurrently, for example, through multi-threaded processing, interrupt processing, or multiple processors, rather than sequentially.

The steps of a method or algorithm described in connection with the embodiments disclosed herein may be embodied directly in a computer or electronic storage, in hardware, in a software module executed by a processor, or in a combination thereof. A software module may reside in a computer storage such as in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a mobile station. In the alternative, the processor and the storage medium may reside as discrete components in a mobile station.

Figure 3:
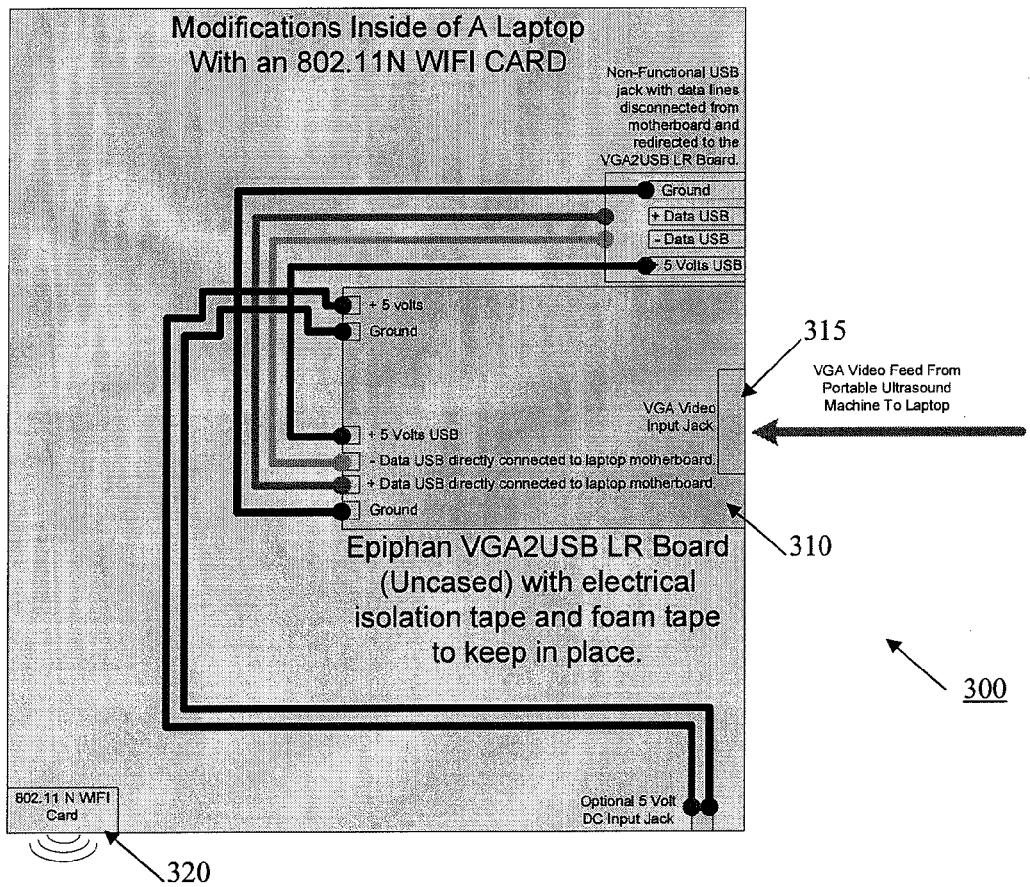
FIG. 3 illustrates a high level circuit diagram of the analog to digital video conversion and communications functions operable within the computer of FIG. 1.

FIG. 3 illustrates a high level circuit diagram 300 of the analog to digital video conversion and communications functions operable within the computer 120. Particularly, the diagram 300 comprises an Epiphan VGA2USB LR board 310 installed within the computer 120. The VGA2USB LR board 310 comprises a VGA video input jack 315 for receiving an analog video feed from the ultrasound system 110. The VGA2USB LR board 310 is coupled to the motherboard (not shown) of the computer 120 through respective positive and negative signal USB connections. The diagram 300 further comprises a 802.11(n) WiFi card 320 that is coupled to the motherboard.

Figure 4:
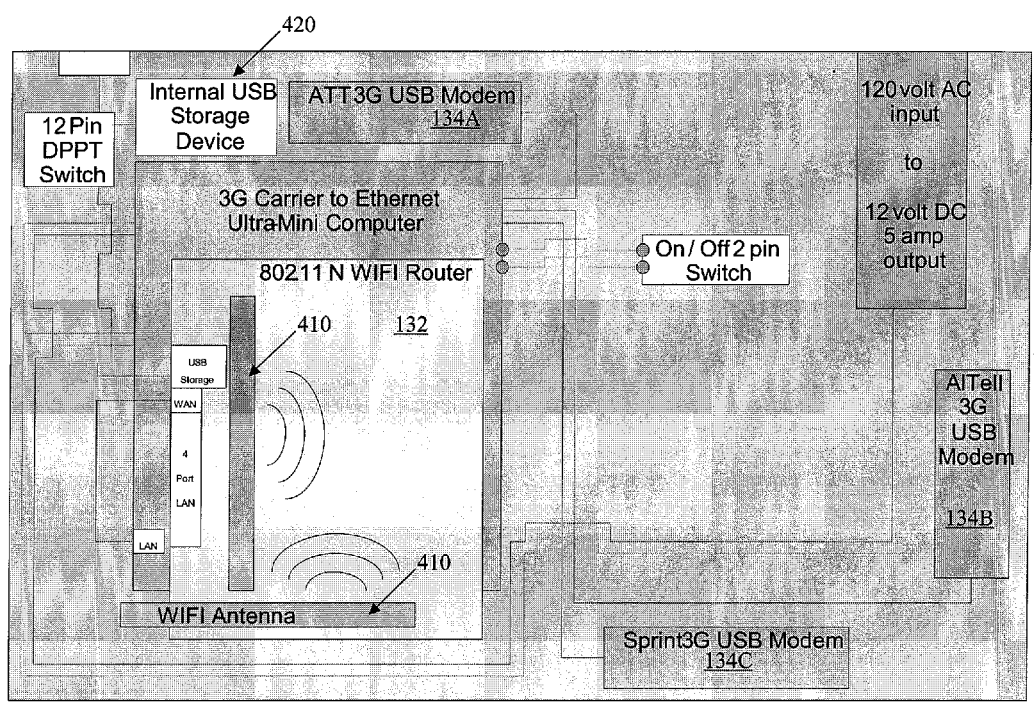
FIG. 4 illustrates the network transceiver shown in FIG. 1 according to an embodiment of the invention.

FIG. 4 illustrates the network transceiver 130 shown in FIG. 1 according to an exemplary embodiment of the invention. The network transceiver 130 comprises an 802.11(n) WiFi router 132 with an antenna array 410, an internal USB storage device 420, and three third generation (3G) cellular modems 134A-C. One of ordinary skill in the art appreciates that the use of 3G is exemplary only. Other mobile and non-mobile communications techniques can be implemented including, but not limited to communications standards such as fourth generation (4G) cellular wireless standards. Moreover, a different number of cellular modems may be implemented. For example, two or four or more cellular modems may be implemented depending on the amount of video data to be transmitted and respective channel bandwidths available. In an exemplary embodiment of the invention, the three 3G cellular modems 134A-C are associated with different cellular broadband networks respectively facilitated by AT&T, AlTell, and Sprint. In an embodiment of the invention, the network transceiver 130 determines the bandwidth available on each respective broadband channel 136 and selects the broadband channels 136 with the highest bandwidths available to optimize the speed and efficiency of the video transmission. In another embodiment of the invention, the broadband channels 136 can include multiple types of broadband media including without limitation various channels related to cellular communications, digital subscriber line (DSL) communications (e.g., GPRS, EDGE, GSM), cable television communications, portable satellite communications, Internet communications, and any combination thereof.

Figure 5:
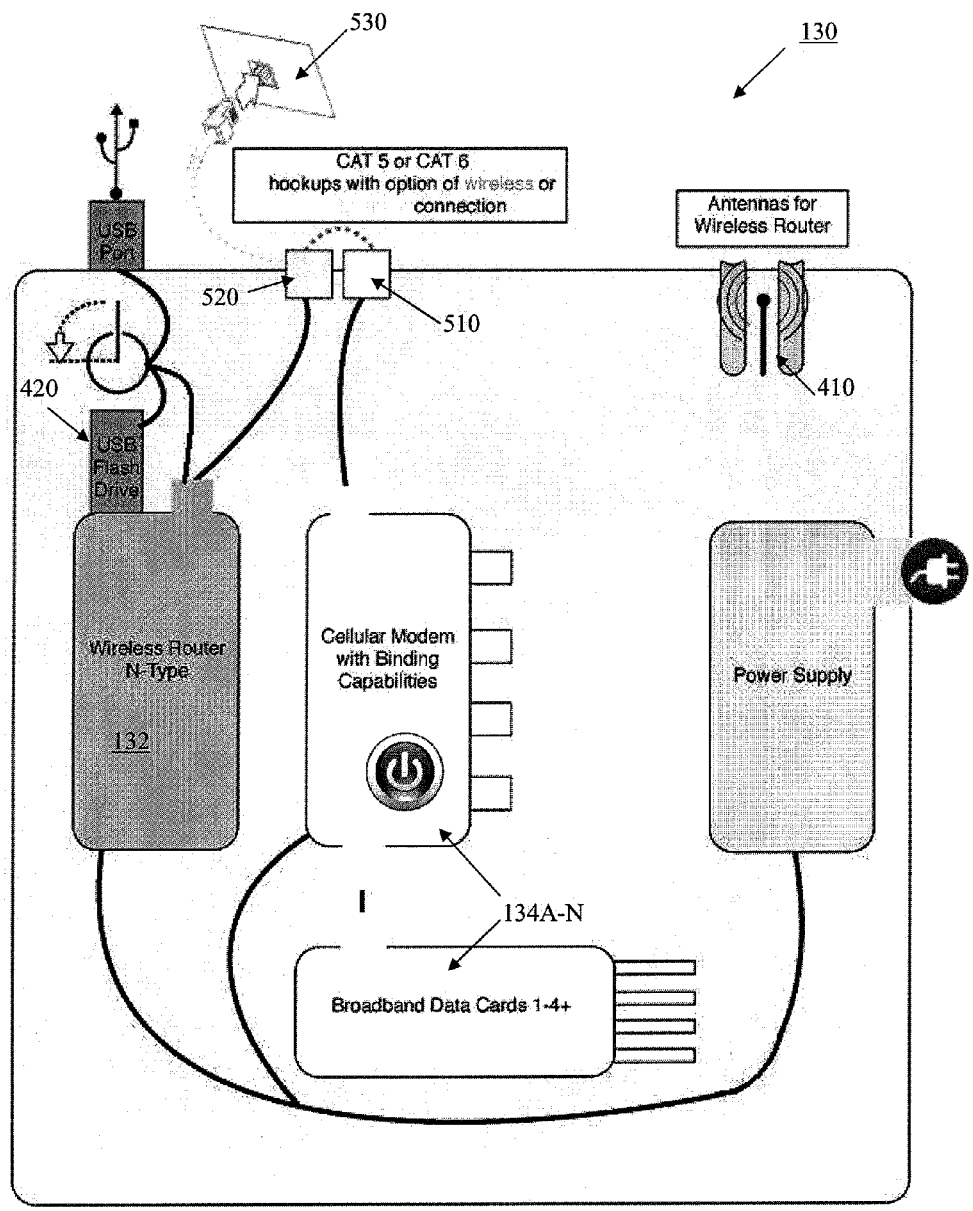
FIG. 5 illustrates the network transceiver according to another embodiment of the invention.

FIG. 5 illustrates the network transceiver 130 according to another embodiment of the invention. Here, the network transceiver 130 comprises the two CAT 5 or CAT 6 connections 510 and 520 mentioned above. Connection 510 attaches to the broadband modems 134A-N and the other connection 520 attaches to the wireless router 132. In an embodiment of the invention, in order to utilize the broadband channels 136A-N, a single cable (not shown) is used to bridge the connections 510 and 520. When an external high-speed internet connection 530 is available, the cable is not connected between the connections 510 and 520. In the latter scenario, a cable is used to connect the connection 520 to the high-speed internet connection 530, which in turn transmits the digital ultrasound video to the web server 150.

To date, real-time ultrasound video transmission has been successfully performed around San Diego, Calif. allowing a sonographer at one location to perform an examination and interact with a veterinary radiologist at a second, remote location using the present invention. The end-result was a complete ultrasound exam performed and viewed in real-time by an off-site radiologist.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

We claim:

1. A method for transmitting a real time ultrasound video feed to a veterinary ultrasound evaluator, the method comprising the steps of:
   acquiring, at a portable ultrasound system, an analog ultrasound video of a veterinary subject at a first location;
   converting, at a portable computer, the analog ultrasound video to a digital ultrasound video;
   transmitting, via a communications link, the digital ultrasound video from the portable computer to a network transceiver, wherein the communications link comprises a IEEE 802.11 communications link,
   processing, at the network transceiver, the digital ultrasound video into multiple streams; and
   transmitting, at the network transceiver, the multiple streams over multiple cellular channels, each cellular channel carrying one of the multiple streams, wherein the multiple cellular channels are facilitated through separate and distinct cellular aircards.

2. The method of claim 1, wherein the analog ultrasound video is formatted according to a VGA format.

3. The method of claim 1, wherein the digital ultrasound video comprises an AVI formatted video or a QuickTime formatted video.

4. The method of claim 1, wherein the step of processing the digital ultrasound video into multiple streams is performed by a broadband bonding network appliance.

5. The method of claim 1, further comprising the steps of:
   aggregating the multiple streams into a reconstituted ultrasound video; and
   making the reconstituted ultrasound video available for display to a veterinary ultrasound evaluator located at a location remote from the first location.

6. A method for transmitting an ultrasound video feed to a veterinary ultrasound evaluator, the method comprising the steps of:
   acquiring, at a portable ultrasound system, an ultrasound video feed of a veterinary subject;
   converting, at a portable computer, the ultrasound video feed to a digital ultrasound video;
   transmitting, via a IEEE 802.11 wireless communications link, the digital ultrasound video to a network transceiver,
   processing, at the network transceiver, the ultrasound video feed into multiple video streams; and
   transmitting, at the network transceiver, the multiple video streams over multiple cellular channels, each cellular channel carrying one of the multiple streams, wherein the multiple cellular channels are facilitated through separate and distinct cellular aircards.

7. The method of claim 6, wherein the acquired video feed is an analog video feed and further comprising the step of converting the analog video feed into a digital video feed.

8. The method of claim 7, wherein the multiple video streams comprise multiple digital video streams.

9. The method of claim 6, further comprising the steps of:
aggregating the multiple video streams into a reconstituted video; and
making the reconstituted video available for display online to a veterinary ultrasound evaluator, wherein the reconstituted video comprises an ultrasound video.

10. A veterinary ultrasound system comprising:
a portable computer comprising an input to acquire an analog ultrasound video of a subject at a first location, an analog-to-digital video conversion card to convert the analog ultrasound video to a digital ultrasound video, and a communications card to transmit the digital ultrasound video via a wireless communications link; and
a network transceiver to receive the digital ultrasound video via the wireless communications link, process the digital ultrasound video into multiple streams, and transmit the multiple streams over multiple cellular channels, each cellular channel carrying one of the multiple streams, wherein the network transceiver comprises a WiFi router and the wireless communications link comprises a WiFi link, and multiple, separate and distinct cellular aircards to facilitate the multiple cellular channels.

11. The system of claim 10, further comprising:
a network server configured to aggregate the multiple streams into a reconstituted ultrasound video; and
a web server configured to make the reconstituted ultrasound video available for display to an evaluator located at a location remote from the first location.

12. The system of claim 10, wherein the network transceiver comprises a broadband bonding network appliance.

13. The system of claim 12, further comprising a switch for bypassing the broadband bonding network appliance.

14. The system of claim 10, wherein the network transceiver comprises data storage.

15. The system of claim 11, wherein the network server comprises a broadband bonding network appliance.

16. The method of claim 1, wherein the separate and distinct cellular aircards are associated with different cellular broadband networks.

17. The method of claim 6, wherein the separate and distinct cellular aircards are associated with different cellular broadband networks.

18. The system of claim 10, wherein the separate and distinct cellular aircards are associated with different cellular broadband networks.

* * * * *